United States Patent [19]

Cullen

[11] Patent Number: 5,312,972

[45] Date of Patent: May 17, 1994

[54] CONVERSION OF HYDROXYMETHYL-IMINODIACETIC ACID TO PHOSPHONOMETHYL-IMINODIACETIC ACID

[75] Inventor: Barry A. Cullen, Lyndeborough, N.H.

[73] Assignee: Hampshire Chemical Corp., Lexington, Mass.

[21] Appl. No.: 969,705

[22] Filed: Oct. 29, 1992

[51] Int. Cl.$^5$ .................. C07C 229/00; C07F 9/38
[52] U.S. Cl. ........................................ 562/17; 562/568
[58] Field of Search ............................ 562/568, 17

[56] References Cited

U.S. PATENT DOCUMENTS

| | | | |
|---|---|---|---|
| 2,331,677 | 10/1943 | Hanslick | 562/568 |
| 4,486,359 | 12/1984 | Hajnóczki | 562/17 |
| 4,724,103 | 2/1988 | Gentilcore | 562/17 |
| 4,921,991 | 5/1990 | Lacroix | 562/17 |
| 4,931,585 | 6/1990 | Pelyva | 562/17 |
| 5,041,628 | 8/1991 | Donadello | 562/17 |

FOREIGN PATENT DOCUMENTS

| | | | |
|---|---|---|---|
| 781212 | 8/1957 | United Kingdom | 562/568 |
| 1142294 | 2/1969 | United Kingdom | 562/17 |

OTHER PUBLICATIONS

Fields, J. Am. Chem. Soc., vol. 74, pp. 1528-1531 (1952).
Weygand, "Preparative Organic Chemistry," pp. 732-736 (1972).

*Primary Examiner*—Michael L. Shippen
*Attorney, Agent, or Firm*—Nields & Lemack

[57] ABSTRACT

A process for preparing N-phosphonomethyl iminodiacetic acid wherein solutions of an alkali metal salt of IDA are reacted with formaldehyde so as to form the alkali metal salt of hydroxymethyliminodiacetic acid (HMIDA). The HMIDA can be subsequently reacted with a phosphorous source such as phosphorous acid to produce PMIDA in good yield.

12 Claims, No Drawings

CONVERSION OF HYDROXYMETHYL-IMINODIACETIC ACID TO PHOSPHONOMETHYL-IMINODIACETIC ACID

BACKGROUND OF THE INVENTION

N-phosphonomethylglycine (glyphosate) is an important broad spectrum herbicide. One conventional precursor to glyphosate is N-phosphonomethyliminodiacetic acid having the following structure:

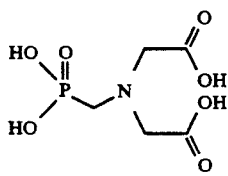

Conventional routes to compound (I) typically involve phosphonomethylating iminodiacetic acid (IDA), the latter obtained by recovering (IDA) from the crude hydrolysate of iminodiacetonitrile (IDAN) by acidification with a mineral acid, crystallization of IDA, filtration thereof, and drying. Such processes result in waste in that the alkali metal salt solution separated from IDA upon the filtration step contains unrecovered IDA. Indeed, fractional crystallization is necessary to precipitate the alkali metal salt, which can then be separated from the IDA solution by centrifugation. In U.S. Pat. No. 3,808,269, disclosed is a process of recovering IDA from an aqueous solution of sodium sulfate and the amino acid by adjusting the pH of the solution to 1.5–3 to form an IDA precipitate and a first mother liquor, and separating and recovering the IDA precipitate therefrom. Sodium sulfate can then be precipitated from the first mother liquor by concentrating the liquor and adjusting the temperature so as to prevent the concomitant precipitation of IDA. The process can then be repeated. However, at some point successive fractional crystallization steps become uneconomical, notwithstanding the presence of additional product in the solution. U.S. Pat. No. 3,852,344 discloses a similar process wherein the sulfuric acid is replaced with hydrochloric acid, with sodium chloride being recovered as the by-product instead of sodium sulfate.

U.S. Pat. No. 5,011,988 discloses an additional process which can be carried out on the waste streams generated from the process of the '269 patent. Thus, the temperature of such waste streams is adjusted so as to precipitate IDA and sodium sulfate decahydrate in the same mother liquor. The mixed crystals are then separated from the mother liquor and recycled to an earlier step in the IDA production process.

As disclosed in U.S. Pat. No. 3,288,846 to Irani, phosphonomethyliminodiacetic acid crystals can be prepared from IDA acid, formaldehyde and phosphorous acid in the presence of hydrochloric acid:

$HN(CH_2CO_2H)_2 + \geq 1H_3PO_3 +$

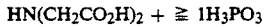
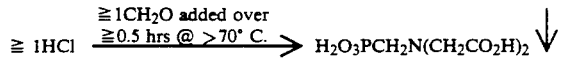

In order to simply the foregoing process, compound (I) can be prepared by hydrolyzing iminodiacetonitrile with an alkali metal base to form an alkalimetal salt of iminodiacetic acid, which is converted to IDA strong acid salt and phosphonomethylated, as disclosed in U.S. Pat. No. 4,724,103. Specifically, the alkali metal salt of IDA is reacted in series first with a strong mineral acid to form the strong acid salt of IDA and the alkali metal salt of the strong acid, and then phosphonomethylated by reacting the strong acid salt of IDA with phosphorous acid and formaldehyde to provide compound (I) and an alkali metal salt. An amount of water sufficient to dissolve the alkali metal salt is added, and compound (I) is separated as a precipitate. Similarly, U.S. Pat. No. 4,775,498 discloses a process for preparing N,N-diacetic acid aminomethylenephosphonic acid by adding phosphorous trichloride to an aqueous solution of a first quantity of an alkali metal salt of IDA and forming a mixture of phosphorous acid and iminodiacetic acid hydrochloride and alkali metal chloride, adding formaldehyde to the mixture while simultaneously adding a second quantity of the alkali metal salt of IDA, adding an amount of water sufficient to dissolve the alkali metal salt, adjusting the pH of the resulting mixture to the isoelectric point of N,N-diacetic acid aminomethylenephosphonic acid, and separating the precipitated acid:

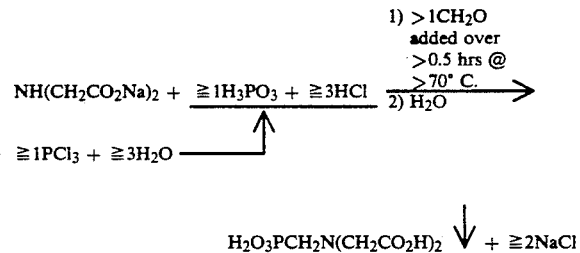

$H_2O_3PCH_2N(CH_2CO_2H)_2 \downarrow + \geq 2NaCl$

However, alkali metal salt solutions of IDA, such as IDANa$_2$, are impractical to store and ship on a commercial scale, as the solubility is only about 22% at room temperature and about 40% at temperatures on the order of 60° C. Even where 40% solubility is acceptable, it is expensive and inconvenient to maintain the high temperatures necessary for such solubility.

It therefore would be desirable to produce phosphonomethyliminodiacetic acid (PMIDA) from an intermediate that can be readily stored and/or shipped at ambient temperature on a commercial scale.

SUMMARY OF THE INVENTION

In accordance with the present invention, there is provided an alternative process for preparing N-phosphonomethyl iminodiacetic acid (I) wherein solutions of an alkali metal salt of IDA are reacted with formaldehyde so as to form the alkali metal salt of hydroxymethyliminodiacetic acid (HMIDA). The HMIDA can be subsequently reacted with a phosphorous source such as phosphorous acid to produce PMIDA in good yield. Surprisingly, the inventor of the present invention has found that hydroxymethyl-IDA reacts readily with phosphorous acid to form PMIDA, especially in view of the prior art teachings that IDA acid/acid salt must be used as the reactant.

DETAILED DESCRIPTION OF THE INVENTION

Preferably the alkali metal salt of IDA used in the process of the present invention is Na$_2$IDA, although other alkali metal salts thereof, such as M$_x$H$_{(2-x)}$IDA (where M is an alkali metal and x is 1 or 2), including but not limited to $K_2IDA$ also may be used. The concentration of the alkali metal IDA used in the instant process should be about 20–40% by weight as IDA acid, preferably about 31% by weight as IDA acid. The alkali metal IDA typically includes about 1% free alkali metal hydroxide present as a result of the formation of the salt from IDA proper from IDAN.

Preferably stoichiometric amounts of formaldehyde are added to the alkali metal IDA, although a mole ratio of IDA to formaldehyde of from about 0.5 to about 2 is suitable. For convenience, formalin (a 44% by weight solution of formaldehyde containing approximately 1% unreacted methanol) can be used to advantage, but other sources of formaldhyde, such as trioxane or paraformaldehyde also can be used. The reaction of alkali metal IDA with the formaldehyde source should be conducted at temperatures below about 70° C., preferably below about 40° C., most preferably between about 30° and 40° C. in order to limit the formation of by-product alkali metal N-methyl-IDA. The formaldehyde can be added over a period of two hours, preferably over about one hour or less, the rate of addition being limited only by the rate at which the heat of reaction can be removed.

The resulting hydroxymethyliminodiacetic acid alkali metal salt solutions are stable at room temperature at up to at least 46.3% concentration (equivalent to 39.6% DSIDA), the highest concentration tested. (Of course higher concentrations are possible.) Accordingly, such solutions can be easily stored and/or shipped on a commercial scale.

The solutions have then been reacted cleanly with a phosphorous acid source, and a strong acid having a $pK_a$ lower than that of phosphorous acid, such as sulfuric acid, hydroiodic acid, hydrobromic acid, hydroxymethylsulfonic acid, preferably hydrochloric acid, to produce phosphonomethyl-IDA. Alternatively, the phosphorus acid and hydrochloric acid can be supplied in the form of $PCl_3$. The reaction scheme is illustrated as follows:

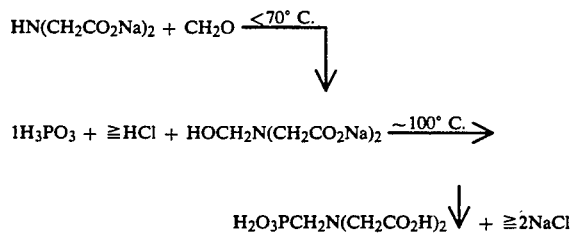

The process can be carried out about 100° C. Lower temperatures result in reduced yield. Even higher yields can be obtained if the process is carried out under slight pressure (e.g., 20–30 psi).

The process of the present invention is illustrated by the following examples. The disodium iminodiacetic acid employed was prepared by reacting 133.1 grams of $IDAH_2$ with 168.9 grams of 50% NaOH and 130 grams of $H_2O$ to form a 41% solution with 1% free NaOH.

EXAMPLE 1

A one mole solution of 48.5% disodium IDA (DSIDA) was prepared and cooled to 40° C. Formaldehyde, 1.2M at 44%, was added to the thick slurry of $DSIDA.6H_2O$ crystals as it cooled in an ice bath to 35° C. Most of the crystals dissolved and reacted to form hydroxymethyl-IDANa$_2$ on stirring overnight at 22° C. Upon warming to 45° C. for 15 minutes, the few remaining crystals dissolved. The resultant 46.3% HMIDA-Na$_2$ solution remained crystal free for over a month at room temperature.

EXAMPLE 2

A 1.0 mole solution of 41% DSIDA was cooled to 40° C. Paraformaldehyde (1.0 mole at 91%) was added to the slurry and heat was applied to maintain 40° C. After about 1 hour, all of the reagents were in solution. The 44.5% HMIDANa$_2$ solution remained crystal free on cooling to room temperature.

EXAMPLE 3

One mole of 41% disodium IDA was charged to a reaction vessel and maintained at 58° C. Over a period of 20 minutes, 87.7 grams (1.3 moles) of 44.45% formaldehyde was added to the vessel. The temperature rose to 61° C.

In a separate one liter reactor, 337.3 grams (3.42 moles) of 37% HCl, 96.4 grams (1.16 moles) 99% $H_3PO_3$ and 50 grams of $H_2O$ were heated to boil. An additional 92 grams of $H_2O$ were added to raise the boiling point above 100° C. Once the temperature reached 100° C., the reaction product of the disodium IDA and formaldehyde, disodium hydroxymethyl-IDA, was added over a period of two hours. The reaction temperature was maintained during that period between 107° and 110° C. The mixture was held an additional two hours, cooled over one hour to 17° C., filtered and washed with 100 ml of ice water. A 70% yield of 100% purity PMIDA was achieved.

EXAMPLE 4

A 41% solution of DSIDA, 432 g (1.00M), containing 1.9% free NaOH was cooled, with stirring, in a 1 liter roundbottom flask and 68.2 g (1.0 mole) of 44% formaldehyde added to the DSIDA slurry over 90 minutes while the temperature was maintained at 30° C. by cooling the flask with a stream of compressed air, as needed. The solution of hydroxymethyl-IDA disodium salt (HMIDANa$_2$) was cooled to room temperature and transferred to a 1 liter erlenmeyer flask.

The 1 liter roundbottom flask was then charged with 35.5 g 37% HCl (0.36M) and 128.9 g 70% $H_3PO_3$ (1.10M). This was heated to the boil and 322.4 g of 37% HCl (3.27M) and 500.2 g of the HMIDANa$_2$ solution (1.00M) pumped separately into the reaction mix over 90 minutes. During this time, 275 g of water was distilled from the reaction flask.

After all of the HMIDA and HCl has been added, the water distillation was stopped and the reagents allowed to reflux while an additional 30.7 g (0.45M) of 44% formaldehyde was added over 10 minutes.

The reaction mass was refluxed an additional 2 hours at which time the 275 g of distillate was returned to the reaction mass followed by cooling to room temperature.

The PMIDA slurry was filtered and the filtercake washed with 50 ml. of water and then dried to yield 190.4 g of PMIDA with a purity of >99%. This is equivalent to an 83% recovery of PMIDA. Analysis of the liquor by LC showed an additional 25.7 g of PMIDA for an overall conversion of 94.7%.

EXAMPLE 5

A 41% solution of DSIDA, 432 g (1.00M), containing 1.9% free NaOH was cooled, with stirring, in a 1 liter roundbottom flask. At 30° C., 51.0 g (0.75M) of 44% formaldehyde was added to the DSIDA slurry over a period of 90 minutes. Temperature was maintained at 30° C. by cooling the flask with a stream of 10 psi compressed air, as needed. The resulting solution of hydroxymethyl-IDA disodium salt (HMIDANa$_2$) was cooled to room temperature and transferred into a 1 liter erlenmeyer flask.

The 1 liter roundbottom flask was then charged with 70 g 37% HCl (0.71M) and 140 g 70% H$_3$PO$_3$ (1.2M). This solution mixture was heated to a boil and 275 g 37% HCl (2.79M) and the HMIDANa$_2$ solution (1.0M) were pumped separately into the reaction mixture over a three hour period. During this feed time, 265 g of water was distilled.

After all the HMIDA and HCl had been added, the reagents were allowed to reflux while an additional 37 g of 44% formaldehyde (0.54M) was fed to the reaction over a convenient thirty minute period.

The reaction mass was held at reflux for an additional four hour hold period. At the completion of the hold period the 265 g of distillate was returned to the reaction mass followed by cooling to room temperature. The PMIDA slurry was filtered and the filter cake was washed with 50 ml. of chilled water then dried to yield 200.6 g of PMIDA with a purity of >99%. This is equivalent to 88.4% recovery of PMIDA. The liquor was analyzed by HPLC and found to contain 1.3% PMIDA which is equivalent to 4.1% yield, for an overall conversion of 92.5%.

EXAMPLE 6

A 41% solution of DSIDA, 432 g (1.00M), containing 1.9% free NaOH was cooled, with stirring, in a 1 liter roundbottom flask. At 30° C., 68.0 g (1.0M) of 44% formaldehyde was added to the DSIDA slurry over a period of 90 minutes. Temperature was maintained at 30° C. by cooling the flask with a stream of 10 psi compressed air, as needed. The resulting solution of hydroxymethyl-IDA disodium salt (HMIDANa$_2$) was cooled to room temperature and transferred into a 1 liter erlenmeyer flask.

A second feed flask, a 500 ml erlenmeyer, was charged with 151.3 g PCl$_3$ (1.10M). The 1 liter roundbottom flask was then charged with 42.4 g H$_2$O. The PCl$_3$ was then fed into the reaction flask at 1.26 g/min. (equivalent to about 120 minutes of feed).

The reaction was started at room temperature. After five minutes of PCl$_3$ feed at 1.26 g. min., the HMIDA-Na$_2$ solution (1.0M) feed was started at 3.7 mls/min. feed (equivalent to about 120 minutes of HMIDANa$_2$ feed). The reaction temperature exothermed to 85° C. before an external heat source was applied to achieve a reflux at 115° C.

After completion of the PCl$_3$ and HMIDANa$_2$ feeds, 18.7 g of 37% HCl was fed to the reaction via the HMIDA feed pump. After this, the reaction was held for a ten minute period, then an additional 0.3M of 44.0% formaldehyde (20.5 g) was fed, below the surface, to the reaction over a thirty minute period (a convenient, non-critical time). The reaction was refluxed for two more hours.

After the reflux period, the reaction was cooled to 25° C. The PMIDA slurry was filtered and the filtercake washed with 50 ml of water, then dried to a yield of 202.0 g of PMIDA, with a purity of 99.8%. This is equivalent to an 89.5% recovery of PMIDA.

What is claimed is:

1. A process for the preparation of a stable, storable solution of an alkali metal salt of hydroxymethyl-iminodiacetic acid, comprising reacting an alkali metal salt of iminodiacetic acid with a formaldehyde source selected from the group consisting of formaldehyde, paraformaldehyde, formalin and trioxane.

2. The process of claim 1 wherein said reaction is carried out at a temperature less than about 70° C.

3. The process of claim 1 wherein said reaction is carried out at a temperature between about 30° and 40° C.

4. The process of claim 1 wherein said alkali metal salt of iminodiacetic acid is the disodium salt.

5. The process of claim 1 wherein said alkali metal salt of iminodiacetic acid is the dipotassium salt.

6. The process of claim 1 wherein said alkali metal salt of iminodiacetic acid is the monosodium salt.

7. The process of claim 1 wherein said alkali metal salt of iminodiacetic acid is the monopotassium salt.

8. The process of claim 1 wherein the mole ratio of iminodiacetic acid to said formaldehyde source is between about 0.5 and 2.

9. The process of claim 1 wherein the mole ratio of iminodiacetic acid to said formaldehyde source is substantially stoichiometric.

10. A process for the preparation of phosphonomethyl-iminodiacetic acid, comprising:

a. reacting an alkali metal salt of iminodiacetic acid with a formaldehyde source selected from the group consisting of formaldehyde, paraformaldehyde, formalin and trioxane to form a stable, storable solution of the alkali metal salt of hydroxymethyl-iminodiacetic acid; and b. reacting the reaction product of step a with a phosphorus source selected from the group consisting of PCl$_3$ and H$_3$PO$_3$ and a strong acid having a pK$_a$ less than or equal to about 2.

11. The process of claim 10 wherein said phosphorous source is phosphorous acid.

12. The process of claim 10 wherein said phosphorous source and strong acid is provided by adding phosphorus trichloride.

* * * * *